US010342884B2

(12) United States Patent
Bettles et al.

(10) Patent No.: US 10,342,884 B2
(45) Date of Patent: *Jul. 9, 2019

(54) ULTRAVIOLET DISINFECTION CASE

(71) Applicant: Sensor Electronic Technology, Inc., Columbia, SC (US)

(72) Inventors: Timothy James Bettles, Irmo, SC (US); Alexander Dobrinsky, Silver Spring, MD (US); Michael Shur, Latham, NY (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/785,687

(22) Filed: Oct. 17, 2017

(65) Prior Publication Data

US 2018/0036444 A1 Feb. 8, 2018

Related U.S. Application Data

(63) Continuation of application No. 14/686,004, filed on Apr. 14, 2015, now Pat. No. 9,801,965, which is a (Continued)

(51) Int. Cl.
*A61L 2/10* (2006.01)

(52) U.S. Cl.
CPC .............. *A61L 2/10* (2013.01); *A61L 2202/14* (2013.01); *A61L 2202/16* (2013.01)

(58) Field of Classification Search
CPC ..... A61L 2/10; A61L 2202/14; A61L 2202/16
(Continued)

(56) References Cited

U.S. PATENT DOCUMENTS

| 4,806,770 A | 2/1989 | Hylton et al. |
| 6,278,122 B1 | 8/2001 | Gagnon |

(Continued)

FOREIGN PATENT DOCUMENTS

| CN | 201046243 Y | 4/2008 |
| EP | 1360932 A1 | 11/2003 |

(Continued)

OTHER PUBLICATIONS

Chinese Application No. 201480016435.3, Office Action3 (with English translation), Feb. 13, 2018, 6 pages.

(Continued)

*Primary Examiner* — Nicole M Ippolito
*Assistant Examiner* — Hanway Chang
(74) *Attorney, Agent, or Firm* — LaBatt, LLC

(57) ABSTRACT

A solution for disinfecting flowable products, such as liquids, suspensions, creams, colloids, emulsions, powders, and/or the like, as well as accessories and products relating thereto, such as containers, caps, brushes, applicators, and/or the like, using ultraviolet radiation is provided. In an embodiment, an ultraviolet impermeable cap is configured to enclose a volume corresponding to a flowable product. At least one ultraviolet radiation source can be mounted on the cap and be configured to generate ultraviolet radiation for disinfecting the enclosed area. The ultraviolet radiation source can be configured to only generate ultraviolet radiation when the volume is enclosed by the ultraviolet impermeable cap.

20 Claims, 14 Drawing Sheets

Related U.S. Application Data continuation-in-part of application No. 14/217,694, filed on Mar. 18, 2014, now Pat. No. 9,006,680.

(60) Provisional application No. 61/802,839, filed on Mar. 18, 2013, provisional application No. 61/939,243, filed on Feb. 12, 2014.

(58) Field of Classification Search
USPC .................. 250/428, 432 R, 433, 434, 435
See application file for complete search history.

(56) References Cited

U.S. PATENT DOCUMENTS

| | | |
|---|---|---|
| 6,458,331 B1 | 10/2002 | Roberts |
| 6,483,119 B1 | 11/2002 | Baus |
| 6,544,727 B1 | 4/2003 | Hei |
| 6,605,260 B1 | 8/2003 | Busted |
| 6,923,367 B1 | 8/2005 | Grossman et al. |
| 7,372,044 B2 | 5/2008 | Ross |
| 7,553,456 B2 | 6/2009 | Gaska et al. |
| 7,634,996 B2 | 12/2009 | Gaska et al. |
| 8,277,734 B2 | 10/2012 | Koudymov et al. |
| 8,318,089 B2 | 11/2012 | Brown-Skrobot et al. |
| 8,330,121 B2 | 12/2012 | Douglas |
| 8,334,521 B2 | 12/2012 | Deshays |
| 8,481,970 B2 | 7/2013 | Cooper et al. |
| 8,980,178 B2 | 3/2015 | Gaska et al. |
| 9,006,680 B2 | 4/2015 | Bettles et al. |
| 9,034,271 B2 | 5/2015 | Shur et al. |
| 9,061,082 B2 | 6/2015 | Gaska et al. |
| 9,138,499 B2 | 9/2015 | Bettles et al. |
| 9,179,703 B2 | 11/2015 | Shur et al. |
| 9,724,441 B2 | 8/2017 | Shur et al. |
| 9,750,830 B2 | 9/2017 | Shur et al. |
| 9,795,699 B2 | 10/2017 | Shur et al. |
| 9,802,840 B2 | 10/2017 | Shturm et al. |
| 9,919,068 B2 | 3/2018 | Shur et al. |
| 9,981,051 B2 | 5/2018 | Shur et al. |
| 2006/0178600 A1 | 8/2006 | Kennedy et al. |
| 2007/0255301 A1 | 11/2007 | Freeman et al. |
| 2010/0061887 A1 | 3/2010 | Harper et al. |
| 2013/0048545 A1 | 2/2013 | Shatalov et al. |
| 2013/0239803 A1 | 9/2013 | Palmer |
| 2014/0202962 A1 | 7/2014 | Bilenko et al. |
| 2015/0217011 A1 | 8/2015 | Bettles et al. |

FOREIGN PATENT DOCUMENTS

| | | |
|---|---|---|
| EP | 1897898 A1 | 3/2008 |
| KR | 20080023244 A | 3/2008 |
| KR | 100951612 B1 | 4/2010 |
| KR | 20110003101 A | 1/2011 |
| KR | 10-2011-0054730 A | 5/2011 |
| KR | 101237462 B1 | 2/2013 |
| KR | 20130135675 A | 12/2013 |
| WO | 2010070432 A1 | 6/2010 |

OTHER PUBLICATIONS

CamelBak, "All Clear UV Purifier," 2012, 8 pages.
Spectroline CB-4000A CellBlaster Operator's Manual, Sep. 2013, 26 pages.
UV Sterilizer for iPhone, printed from http://www.sinco-elec.com/e_products/Portable-UV-Sterilizer-for-iPhoneiPod-p126.html on Dec. 17, 2013.
UV Light Sterilizer Cell Phone iPode iPhone ear bud Sanitizer—Keeps Electronic Devices Germ Free!, printed from http://www.ankaka.com/uv-light-sterilizer-cell-phone-ipod-iphone-ear-bud-sanitizer-keeps-electronic-devices-germ-free_p48896.html on Dec. 17, 2013.
Chang, H., U.S. Appl. No. 14/686,004, Notice of Allowance, dated Jun. 27, 2017, 11 pages.
Chang, H., U.S. Appl. No. 14/686,004, Non-Final Rejection, dated Jan. 27, 2017, 5 pages.
Chang, H., U.S. Appl. No. 14/686,004, Final Reject, dated Aug. 9, 2016, 9 pages.
Chang, H., U.S. Appl. No. 14/686,004, dated Feb. 26, 2016, 11 pages.
Wells, N., U.S. Appl. No. 14/217,694, Notice of Allowance, dated Nov. 28, 2014, 21 pages.
Chinese Application No. 201480016435.3, Office Action2 (with English translation), Jul. 31, 2017, 11 pages.
Chinese Application No. 201480016435.3, Office Action1 (with English translation), dated Jan. 25, 2017, 19 pages.
German Application No. 11 2014 001 503.2, Office Action1 (English translation is not available), dated Apr. 3, 2017, dated May 16, 2017, 12 pages.
Han, I., International Application No. PCT/US2014/030962, International Search Report and Written Opinion, dated Oct. 10, 2014, 12 pages.

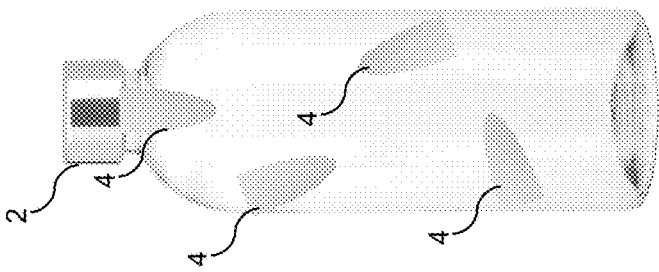
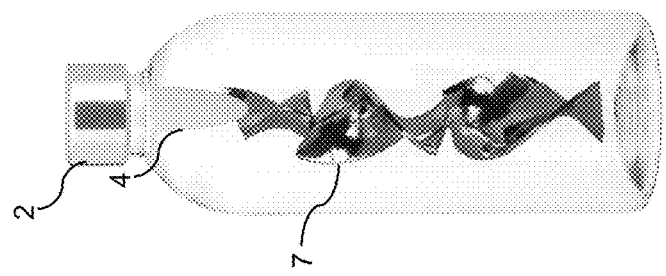
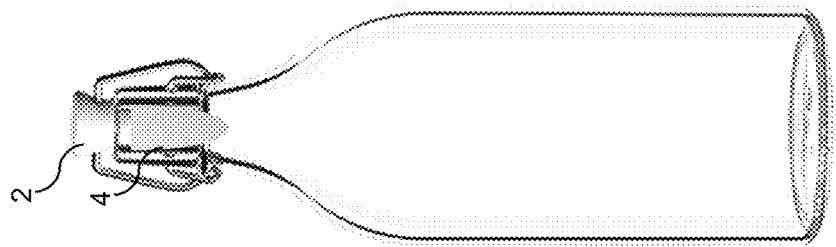

ULTRAVIOLET DISINFECTION CASE

REFERENCE TO RELATED APPLICATION

The current application is a continuation of U.S. application Ser. No. 14/686,004, entitled "Ultraviolet Disinfection Case," filed on 14 Apr. 2015, which is a continuation-in-part of U.S. application Ser. No. 14/217,694, filed on 18 Mar. 2014, now U.S. Pat. No. 9,006,680, which claims the benefit of U.S. Provisional Application No. 61/802,839, filed on 18 Mar. 2013, and U.S. Provisional Application No. 61/939,243, filed on 12 Feb. 2014, each of which is hereby incorporated by reference in its entirety to provide continuity of disclosure.

TECHNICAL FIELD

The disclosure relates generally to ultraviolet radiation, and more particularly, to a device including one or more ultraviolet emitters mounted thereto for disinfecting a flowable product, such as a liquid, a suspension, a cream, a colloid, an emulsion, a powder, and/or the like, as well as flowable products relating thereto, such as containers, caps, brushes, applicators, and/or the like.

BACKGROUND ART

Ultraviolet (UV) radiation has been utilized to sanitize different devices. For example, there is an approach for sanitizing toothbrushes using UV light. In this approach, an apparatus includes a UV lamp of low intensity for emitting UV radiation in the 200 to 300 nanometer wavelength range, as well as some radiation in the visible range above 300 nanometers and in the ozone producing range below 200 nanometers.

Other sanitizing devices are also known in the art. For example, one approach proposes a mailbox enclosure to sanitize mail articles with UV light and other means. Another approach proposes a surgical tool sterilizing enclosure that utilizes UV light as well as chemical and other sanitizing agents.

Other approaches include a computer input device sterilization apparatus including UV sterilization in an enclosed container to kill bacteria and other disease carrying organisms. One approach includes a horizontal or vertical container dimensioned to fit over computer input devices such as keyboards, mice, trackballs, touchpads and the like. A UV source located within the container irradiates the computer input device with UV light which generates ozone gas, thereby killing any microorganisms that might reside on the computer input device. UV radiation below 200 nm can also be used to create ozone gas having germicidal characteristics. The ozone gas is circulated in and around the input device(s) to provide further sterilization with the UV radiation. A sterilization switch turns the UV source off when the container is opened. A timer/power circuit provides a timed application of power to the UV lamps to provide UV illumination consistent with the substantial sterilization of the input device in question.

There are currently also UV devices available to sterilize mobile phones, such as the UV Sterilizer for the iPhone® from Sinco-Electronic Gifts Co., which is a desktop unit. In this case, a user places his/her phone into the sterilizer for approximately five minutes. The device turns a blue light emitting diode (LED) on to indicate the start of the sterilization process. Once the blue LED turns of, the sterilization process is complete. Such devices typically utilize mercury lamps to generate the ultraviolet light.

SUMMARY OF THE INVENTION

In view of the prior art, the inventors have identified many challenges and limitations of current approaches for disinfecting various commonly used flowable products using ultraviolet radiation. For example, the inventors have noted that current approaches are not designed to disinfect some types of commonly used flowable products, such as liquids, suspensions, creams, colloids, emulsions, powders, and/or the like, as well as accessories and products relating thereto, such as containers (e.g., cases), covers (e.g., caps), brushes, applicators, and/or the like.

Aspects of the invention provide a solution including ultraviolet disinfection of a flowable product. For example, an embodiment includes an ultraviolet radiation containing case configured to enclose a volume corresponding to a flowable product. In an illustrative embodiment, at least one ultraviolet radiation source is configured to generate ultraviolet radiation for disinfecting the enclosed volume. The ultraviolet radiation source can be configured to only generate ultraviolet radiation when the volume is enclosed by a cover so that there is no risk that the user of the flowable product could be harmed.

A first aspect of the invention provides an apparatus comprising: an ultraviolet radiation containing case configured to enclose a volume corresponding to a flowable product, wherein the flowable product can be accessed when the case is open; a cover configured to selectively close and open the case; at least one ultraviolet radiation source mounted on at least one of: the case or the cover, the at least one ultraviolet radiation source configured to generate ultraviolet radiation for disinfecting the volume corresponding to the flowable product; and a sensor configured to cause the at least one ultraviolet radiation source to turn off when the volume is not closed.

A second aspect of the invention provides a system comprising: a container comprising: a first compartment including a first portion of a flowable product; a second compartment including a second portion of the flowable product; and at least one one-way channel for transferring a portion of the flowable product from the first compartment to the second compartment; an ultraviolet impermeable cover configured to enclose a volume of the container, wherein the volume includes the second compartment; at least one ultraviolet radiation source, the at least one ultraviolet radiation source configured to generate ultraviolet radiation for disinfecting the volume of the container; and a sensor located between the cover and the container, the sensor configured to cause the at least one ultraviolet radiation source to turn off when the volume is not enclosed.

A third aspect of the invention provides a system comprising: an ultraviolet radiation containing case including a flowable product stored therein; means for generating ultraviolet radiation to disinfect the flowable product; and means for controlling the generating of the ultraviolet radiation.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description

FIG. 4A shows a cross sectional view of an illustrative system according to an embodiment, while

FIG. 5A shows a side view of an illustrative system according to an embodiment, while

FIG. 6A shows a cross sectional view of an illustrative system according to an embodiment, while

FIGS. 10A-10C show illustrative flowable products for use with an ultraviolet radiation system according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
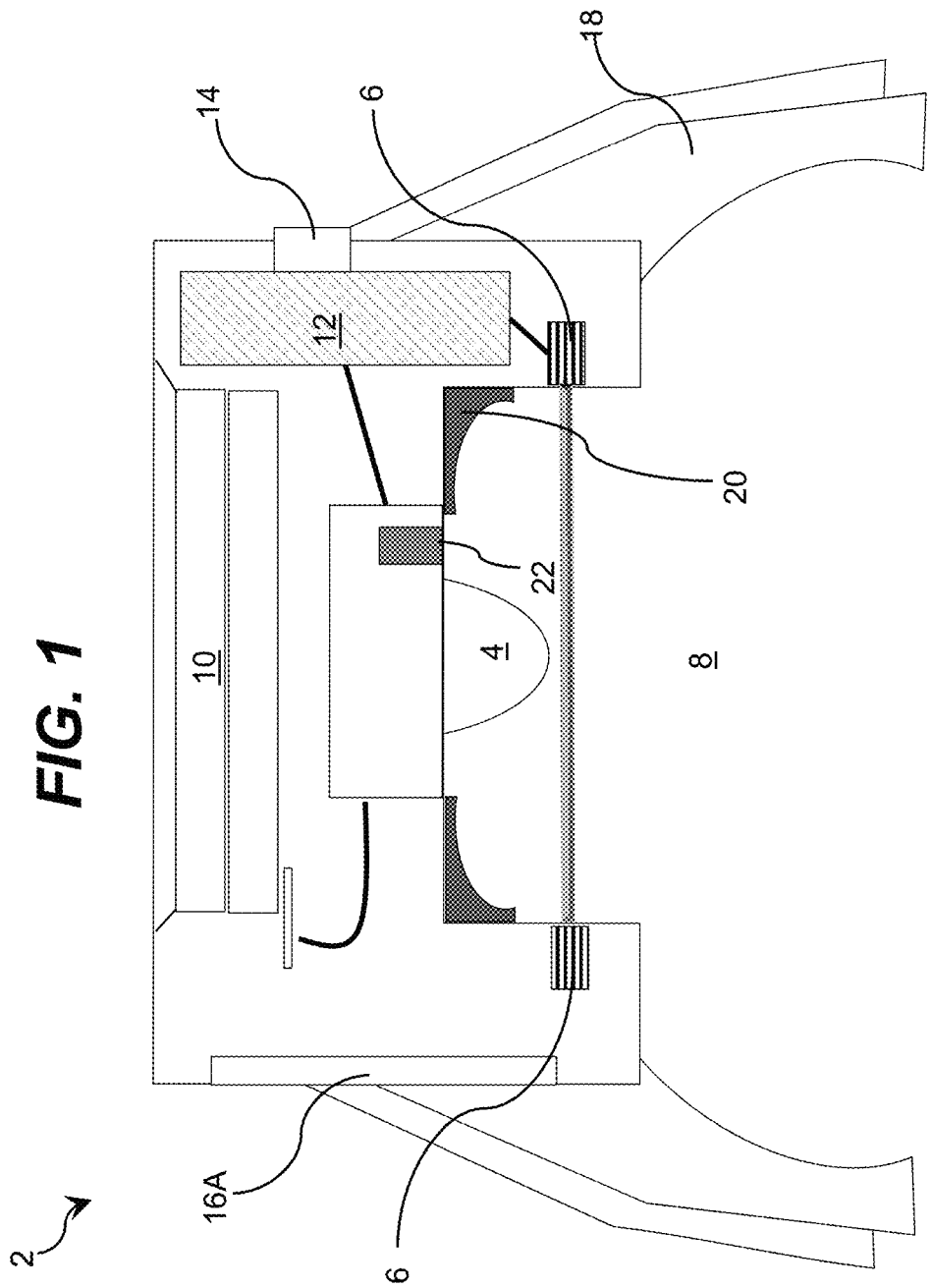
FIG. 1 shows a cross sectional view of an illustrative ultraviolet impermeable cap including ultraviolet radiation source(s) according to an embodiment.

As indicated above, aspects of the invention provide a solution for disinfecting flowable products using ultraviolet radiation. As used herein, a flowable product is any product that includes liquids, suspensions, creams, colloids, emulsions, powders, and/or the like. In addition, a flowable product includes any accessories or ancillary products used in conjunction with the liquids, suspensions, creams, colloids, emulsions, powders, and/or the like, including containers (e.g., cases), covers (e.g., caps), brushes, applicators, and/or the like. In an embodiment, an ultraviolet impermeable cover (also referred to as a cap) is configured to enclose a volume corresponding to a flowable product (e.g., where the flowable product is stored, an area formed by the flowable product, and/or the like). In an illustrative embodiment, at least one ultraviolet radiation source is configured to generate ultraviolet radiation for disinfecting the enclosed area, and can be mounted on the case and/or cover. A sensor can be located between the case and the cover and be configured to cause the at least one ultraviolet radiation source to turn off (or equivalently not turn on) when the area is not enclosed.

As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately ten nanometers (nm) to approximately four hundred nm, while ultraviolet-C (UV-C) means electromagnetic radiation having a wavelength ranging from approximately one hundred nm to approximately two hundred eighty nm, ultraviolet-B (UV-B) means electromagnetic radiation having a wavelength ranging from approximately two hundred eighty to approximately three hundred fifteen nanometers, and ultraviolet-A (UV-A) means electromagnetic radiation having a wavelength ranging from approximately three hundred fifteen to approximately four hundred nanometers. As also used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through (e.g., at least ten percent of the ultraviolet light radiated at a normal incidence to an interface of the material/structure).

As used herein, the term "disinfection" and its related terms means treating an area, which can include interior surfaces forming the area, a portion of a flowable product present in the area, and/or the like, so that the area includes a sufficiently low number of contaminants (e.g., chemical) and microorganisms (e.g., virus, bacteria, and/or the like) to allow the flowable product to be handled as part of a desired human interaction with no or no reasonable risk for the transmission of a disease or other harm to the human. For example, disinfection of an area means that the area (including some portion of the flowable product) has a sufficiently low level of active microorganisms and/or concentration of other contaminants that a typical human can handle the flowable product without suffering adverse effects from the microorganisms and/or contaminants present on the flowable product and/or within the area. In addition, disinfection can include sterilization. As used herein, the term "sterilization" and its related terms means neutralizing an ability of a microorganism to reproduce, which may be accomplished without physically destroying the microorganism. In this example, a level of microorganisms present on and/or in the area cannot increase to a dangerous level and will eventually be reduced, since the replication ability has been neutralized. A target level of microorganisms and/or contaminants can be defined, for example, by a standards setting organization, such as a governmental organization.

Turning to the drawings, FIG. 1 shows a cross sectional view of an ultraviolet impermeable cap 2 according to an embodiment. The ultraviolet impermeable cap 2 is configured to enclose a volume 8 corresponding to a flowable product and can include one or more surfaces reflective of and/or absorbing of ultraviolet radiation. For example, the volume 8 can correspond to an interior of a case within which the flowable product is stored, an area where a portion of the flowable product is exposed, and/or the like. Ultraviolet radiation source(s) 4 can be mounted on the ultraviolet impermeable cap 2 using any solution. The ultraviolet radiation source(s) 4 can comprise any combination of one or more visible and/or ultraviolet radiation emitters. For example, the ultraviolet radiation source 4 can include a high intensity ultraviolet lamp (e.g., a high intensity mercury lamp), an ultraviolet light emitting diode (LED), super luminescent LEDs, laser diodes, and/or the like. In an embodiment, the ultraviolet radiation source 4 includes a set of light emitting diodes manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). In an illustrative embodiment, the ultraviolet radiation source 4 can emit ultraviolet radiation in the range of approximately 200 nanometers to approximately 340 nanometers. Additionally, the ultraviolet radiation source 4 and/or ultraviolet impermeable cap 2 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, within the volume 8. Illustrative wave guiding structures include, but are not limited to, a plurality of ultraviolet fibers, each of which terminates at an opening, a diffuser, and/or the like. The ultraviolet impermeable cap 2 can include a plurality of sockets for the ultraviolet radiation sources 4. The sockets allow for the removal and insertion of the ultraviolet radiation sources 4. The ultraviolet radiation sources 4 can be powered by a power source 10 (e.g., one or more batteries), which is also located within the ultraviolet impermeable cap 2.

The ultraviolet impermeable cap 2 can be configured to disinfect the enclosed volume 8 corresponding to the flowable product. As mentioned herein, in an embodiment, flowable products can include liquids, suspensions, creams, colloids, emulsions, powders, and/or the like, as well as items relating thereto, such as containers (e.g., cases), covers (e.g., caps), brushes, applicators, and/or the like. For example, the flowable product can include a tube of toothpaste, a lipstick, a cosmetic powder case, a container of cream, an eyeliner pencil, and/or the like. As such, the volume corresponding to the flowable product can be the opening of such products used by a user to access the flowable product. Additionally, the flowable product can also include an eyelash brush, a cosmetic brush, and/or the like. The volume corresponding to such flowable products can a portion of the item on which the flowable product is applied to facilitate use by a user (e.g., the bristles of the eyelash brush or the cosmetic brush).

The ultraviolet impermeable cap 2 can include a sensor 6 configured to sense when the volume 8 corresponding to the flowable product is enclosed by the ultraviolet impermeable cap 2. The sensor 6 can be located between the ultraviolet impermeable cap 2 and the flowable product (within the volume 8). The sensor 6 can be connected, e.g., by a wireless or wired communication channel, to a control system 12 that manages the ultraviolet radiation generated by the ultraviolet radiation source(s) 4. The control system 12 can include an ultraviolet radiation indicator 14 that indicates to a user when ultraviolet radiation is being generated.

The ultraviolet impermeable cap 2 can also include an external interface 16A. The external interface 16A can include an interface device, such as a display, which provides a plurality of statistical information regarding the flowable product to a user. The statistical information can be used by the user to, for example, estimate a lifetime for the flowable product. For example, the statistical information can include a number of times the flowable product was disinfected, a number of times the flowable product was used, a frequency of usage, and/or the like. The external interface 16A can include a touch screen display that would allow the user to control one or more aspects of the operation of the ultraviolet radiation source(s) 4.

The ultraviolet impermeable cap can be thermally managed through a plurality of wings 18. The wings 18 are designed to dispose of excess heat generated by the ultraviolet radiation source(s) 4, e.g., using air convective cooling. The wings 18 can be made out of, for example, conductive metals such as aluminum or aluminum alloy in order to facilitate the heat transfer from the cap 2 to the surrounding ambient. In addition, the ultraviolet impermeable cap 2 can comprise at least one reflector 20 mounted to an interior surface of the ultraviolet impermeable cap 2. The reflector 20 can include a reflective material, such as highly polished aluminum, a polytetrafluoroethylene (PTFE, such as Teflon), a highly ultraviolet reflective expanding polytetrafluoroethylene (ePTFE) membrane (e.g., GORE® Diffuse Reflector Material), and/or the like, that reflects at least fifty percent of the ultraviolet radiation.

The ultraviolet impermeable cap 2 can also include a sensor 22 for obtaining attribute information regarding the flowable product and/or the volume 8 for feedback to the control system 12. The control system 12 can use the attribute information to manage the ultraviolet radiation generated by the ultraviolet radiation source(s) 4 using any solution.

Figure 2A:
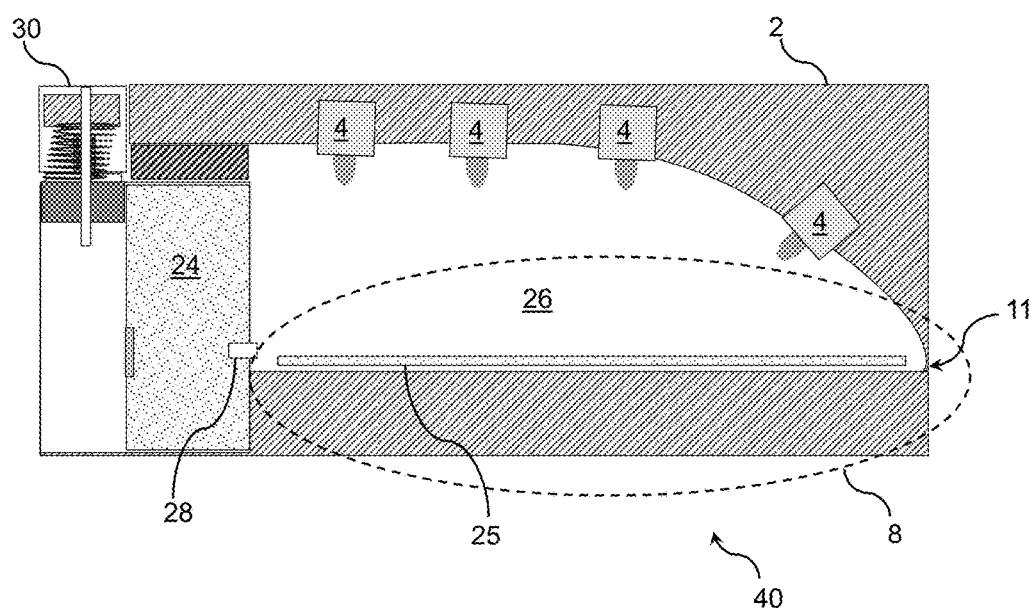
FIG. 2A shows a cross sectional view of an illustrative system according to an embodiment.

In an embodiment shown in FIG. 2A, the ultraviolet impermeable cap 2 can enclose a volume 8 of an ultraviolet radiation containing case or container 40. The container 40 can be configured to contain a flowable product (e.g., liquid, colloid, emulsion, suspension, powder, cream, and/or the like). The container 40 can include a first compartment 24 and a second compartment 26. A first portion of the flowable product is stored within the first compartment 24. A one-way channel 28 is provided for transferring a second portion 25 of the flowable product from the first compartment 24 to the second compartment 26. In an embodiment, the second compartment 26 contains only a small percentage of the overall product, e.g., an amount in a range from 0.1 to 5%. It is understood that the container 40 can include any number of one-way channels 28. The one-way channel 28 can include a valve for preventing the flowable product from transferring from the second compartment 26 to the first compartment 24. Alternatively, the one-way channel 28 can be positioned in a location between the compartments 24, 26 where a level of the product within the second compartment 26 would not be high enough to transfer to the first compartment 24. In an embodiment, the first compartment 24 is inaccessible to a user, and therefore, is less likely to be contaminated. However, the second compartment 26 is accessible to a user and therefore disinfection may be desired. The second compartment 26 (and the portion 25 of the flowable product in the second compartment 26) are within the enclosed volume 8 and can be disinfected by the ultraviolet radiation source(s) 4. In the embodiment shown in FIG. 2A, the portion 25 of the flowable product can be transferred to the second compartment 26 via a pump 30.

Figure 2B:
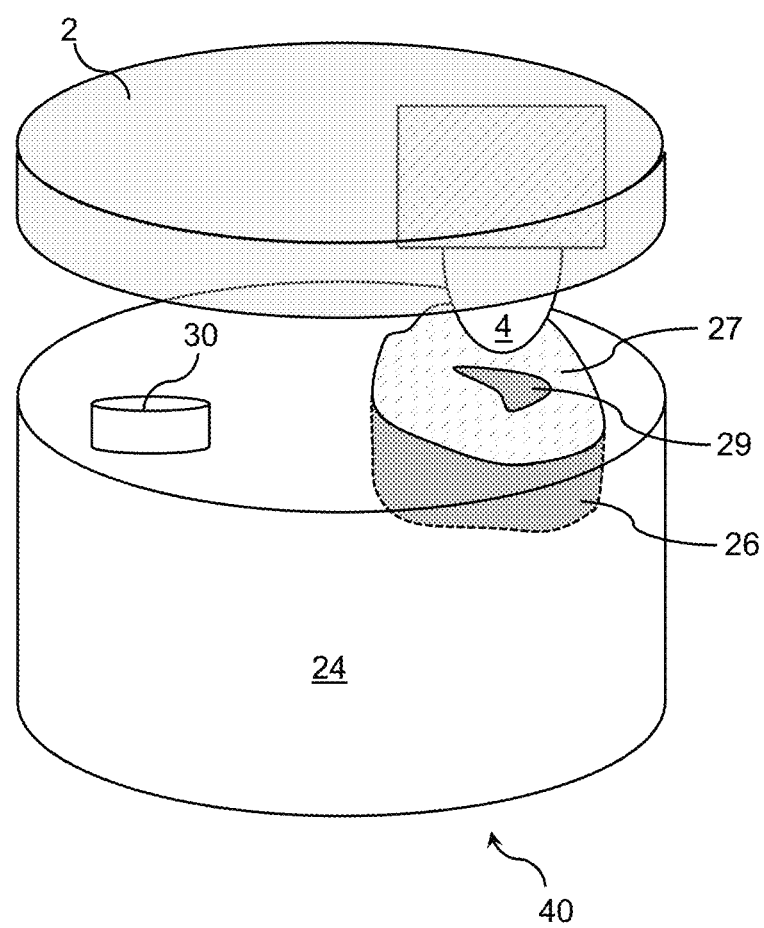
FIG. 2B shows an illustrative container according to an embodiment.

FIG. 2B shows an illustrative container 40 according to an embodiment, which can be implemented as part of a system described herein. In this case, the container 40 is configured to store a flowable product (e.g., a cream or the like), for which disinfection is desired. The flowable product can be extracted from the container 40 by, for example, a pumping device 30 or the like. For example, the pumping device 30 can be operated to transfer the flowable product from a first compartment 24, which is configured to store a large fraction of the flowable product, to a second compartment 26, which contains only a small fraction of the flowable product (e.g., an amount of the flowable product typically utilized in a single use).

The second compartment 26 can have a cover 27 at least partially fabricated of an ultraviolet transparent material. Suitable illustrative ultraviolet transparent materials for the cover 27 include fluoropolymers, such as: fluorinated ethylene propylene (FEP), ethylene FEP (EFEP), polytetrafluoroethylene (PTFE), ethylene chlorotrifluoroethylene (ECTFE), polychlorotrifluoroethene (PCTFE), perfluoroalkoxy alkane (PFA), polyvinylidene fluoride (PVDF), ethylene tetrafluoroethylene (ETFE), tetrahydrocannabivarin (THV), THE, polylactic acid (PLA), low-density polyethylene (LDPE), MFA, and/or the like. The cover 27 can include a set of openings, which allow the flowable product 29 to be extracted from the second compartment 26, e.g., by applying pressure to the second compartment 26. The set of openings can include a number of openings of a particular size, which can be selected based on the flowable product 29 using any solution. While the cover 27 is shown located on the top of the second compartment 26, it is understood that any portion of the second compartment can be fabricated using an ultraviolet transparent material.

The cap 2 can be attached to the container 40 using any solution, e.g., a screw thread. The cap 2 can include a set of ultraviolet radiation sources 4, which, when the cap 2 is securely attached to the container 40, are positioned in a manner that ultraviolet radiation is directed at the ultraviolet transparent cover 27 and the opening(s) and/or flowable product 29 present thereon. As a result, at least some of the ultraviolet radiation will pass through the ultraviolet material forming the cover 27 and into the second compartment 26 and/or flowable product 29 present in the second compartment 26. In this manner, the ultraviolet radiation source(s) 4 can be operated as described herein to disinfect the portions of the flowable product 29 and/or the container 40 most susceptible to contamination.

Figure 3:
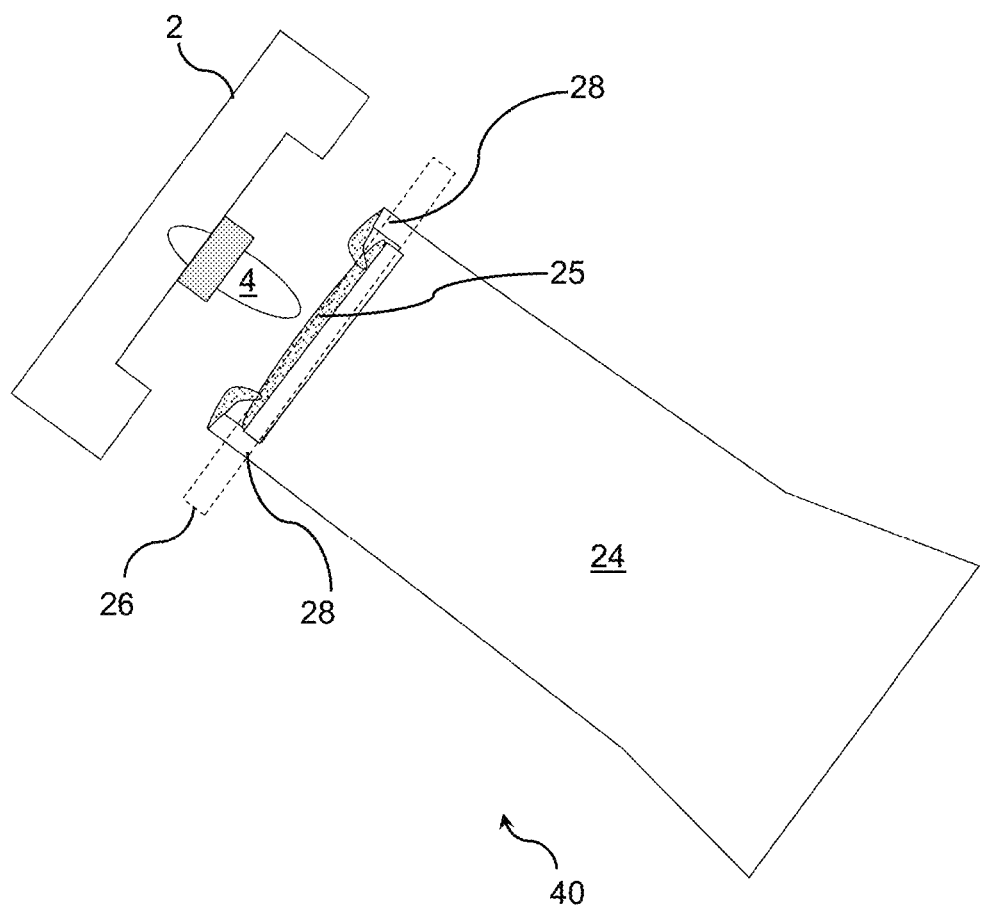
FIG. 3 shows a side view of an illustrative system according to an embodiment.
Figure 4A:
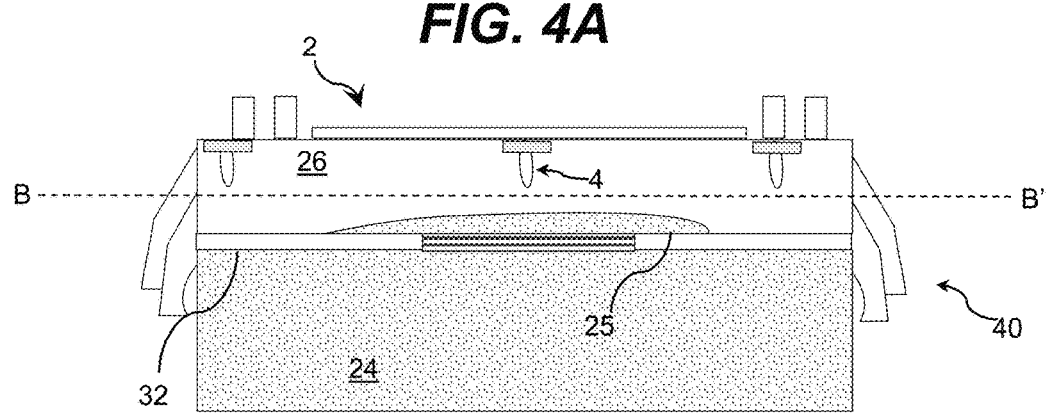
Figure 4B:
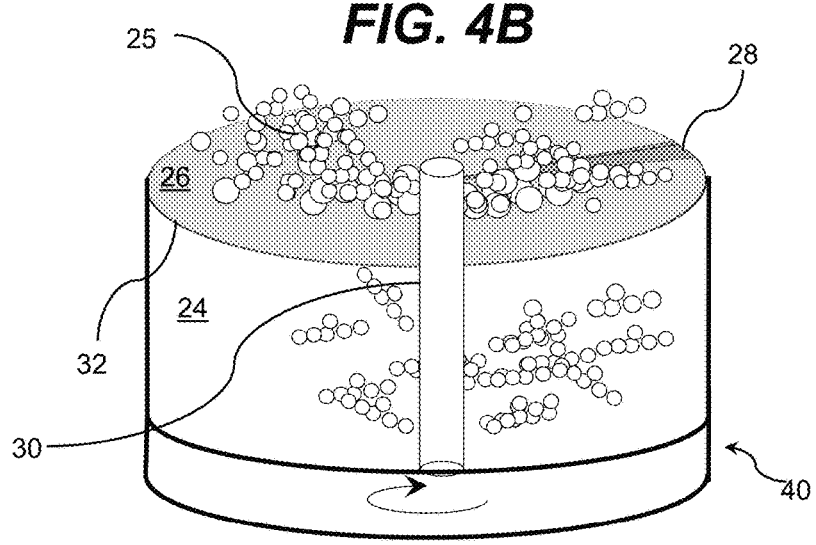
FIG. 4B shows an isometric top view of an illustrative system according to an embodiment.

In an alternative embodiment, as seen in FIG. 3, the portion 25 of the flowable product can be transferred to the second compartment 26 by an increase in pressure in the first compartment 24 (e.g., via a user squeezing the first compartment 24) so that the portion 25 of the product is transferred through two one-way channels 28 to the second compartment 26. In another embodiment, as seen in FIGS. 4A and 4B, a rotating auger 30 can transfer the portion 25 of the product from the first compartment 24 to the second compartment 26. A one-way channel 28 allows for the portion 25 of the flowable product to transfer to the second compartment 26 by rotating the auger 30 so that a plate 32 that separates the first compartment 24 and the second compartment 26 simultaneously rotates and lowers. This can push the portion 25 of the flowable product through the one-way channel 28 and into the second compartment 26.

Figure 5A:
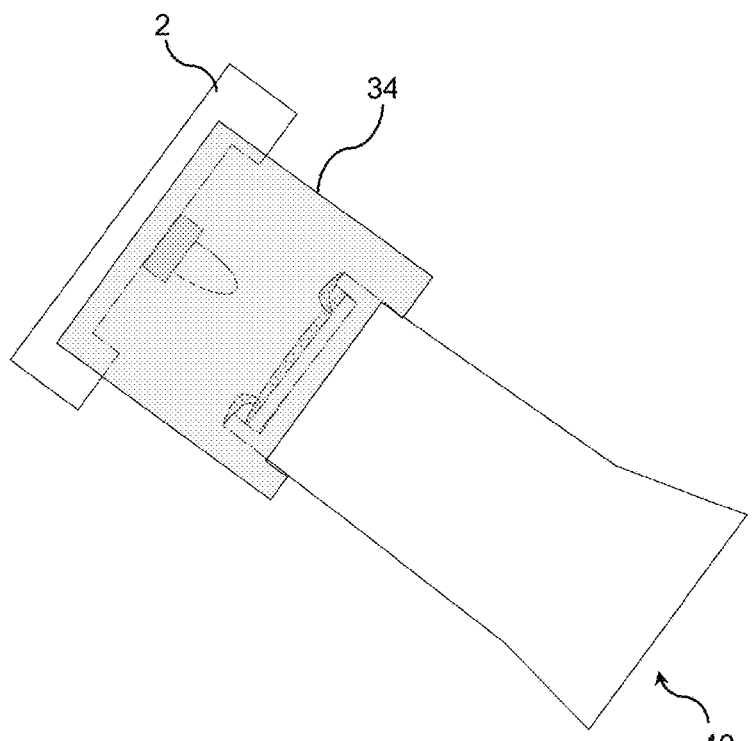
Figure 5B:
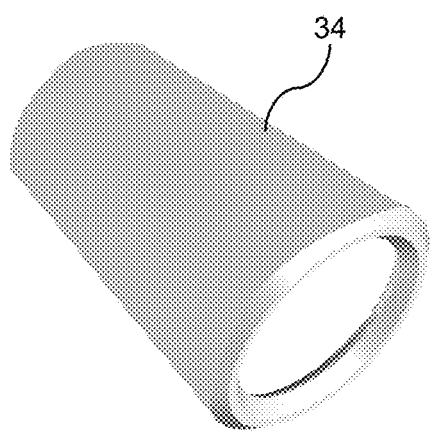
FIG. 5B shows an isometric view of an interconnect according to an embodiment.

The ultraviolet impermeable cap 2 can be manufactured to be any size to fit any type of container corresponding to a flowable product for disinfection. The ultraviolet impermeable cap 2 can connect to the flowable product using any means. For example, the ultraviolet impermeable cap 2 can include threading that fastens to threading on the container corresponding to the flowable product. In an embodiment, the ultraviolet impermeable cap 2 can be hingedly connected via a hinge 11 to a flowable product (e.g., container 40 as shown in FIG. 2A). In another embodiment, as seen in FIGS. 5A and 5B, the ultraviolet impermeable cap 2 can include an interconnect 34 that is made of a flexible material (e.g., rubber) so that at least a portion of the flowable product (e.g., container 40) can be inserted easily into the interconnect 34. Furthermore, the ultraviolet impermeable cap 2 can be connected to the interconnect 34 using any solution.

Figure 6A:
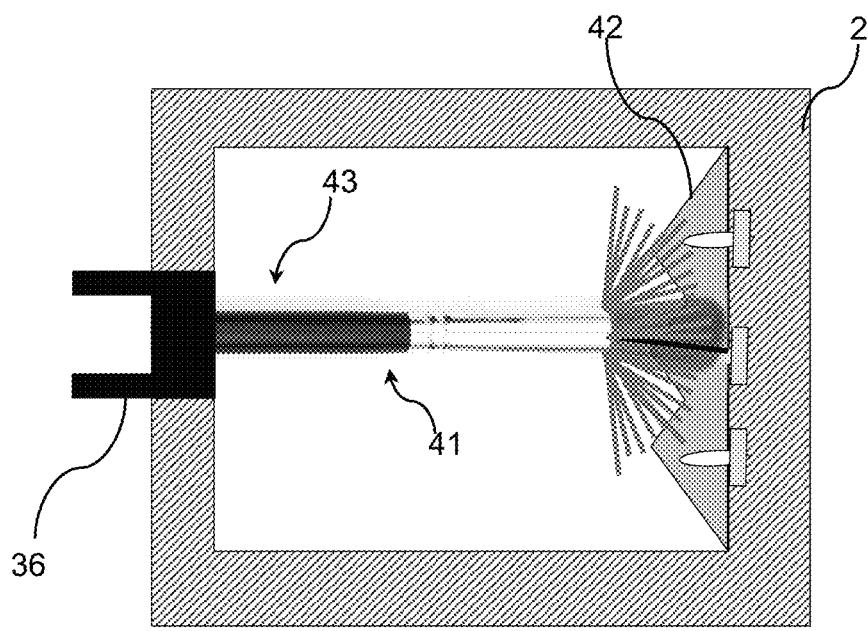
Figure 6B:
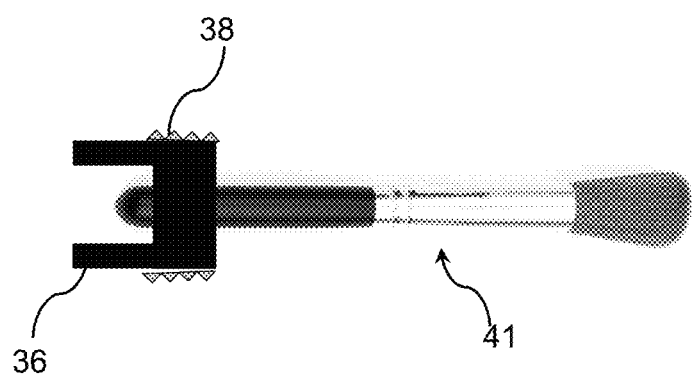
FIG. 6B shows a side view of an illustrative flowable product including a handle assembly according to an embodiment.

In an embodiment, the flowable product may not include a container having an opening with threading, and/or the like, for attaching an ultraviolet impermeable cap. In this situation, a case can form substantially all of an enclosure corresponding to the flowable product within which a volume corresponding to the flowable product can be disinfected. For example, in FIGS. 6A and 6B, a handle assembly 36 is provided for the flowable product 41 (e.g., a cosmetic brush). A handle end 43 of the flowable product 41 can be inserted into the handle assembly 36 using any solution. For example, the handle assembly 36 can be made of a flexible material, such as rubber, to accommodate multiple size handle ends 43. The handle assembly 36 can include a fastening mechanism 38 (e.g., threading) for attaching an ultraviolet radiation absorbing case 2 to the handle assembly 36. Therefore, the ultraviolet radiation absorbing case 2 can enclose and disinfect a volume within which a portion of the flowable product 41 is located. In a more specific embodiment, the ultraviolet radiation absorbing case 2 can also include a rough element 42 for separating the bristles of the flowable product 41 (e.g., a cosmetic brush) to efficiently disinfect the bristles.

Figure 7:
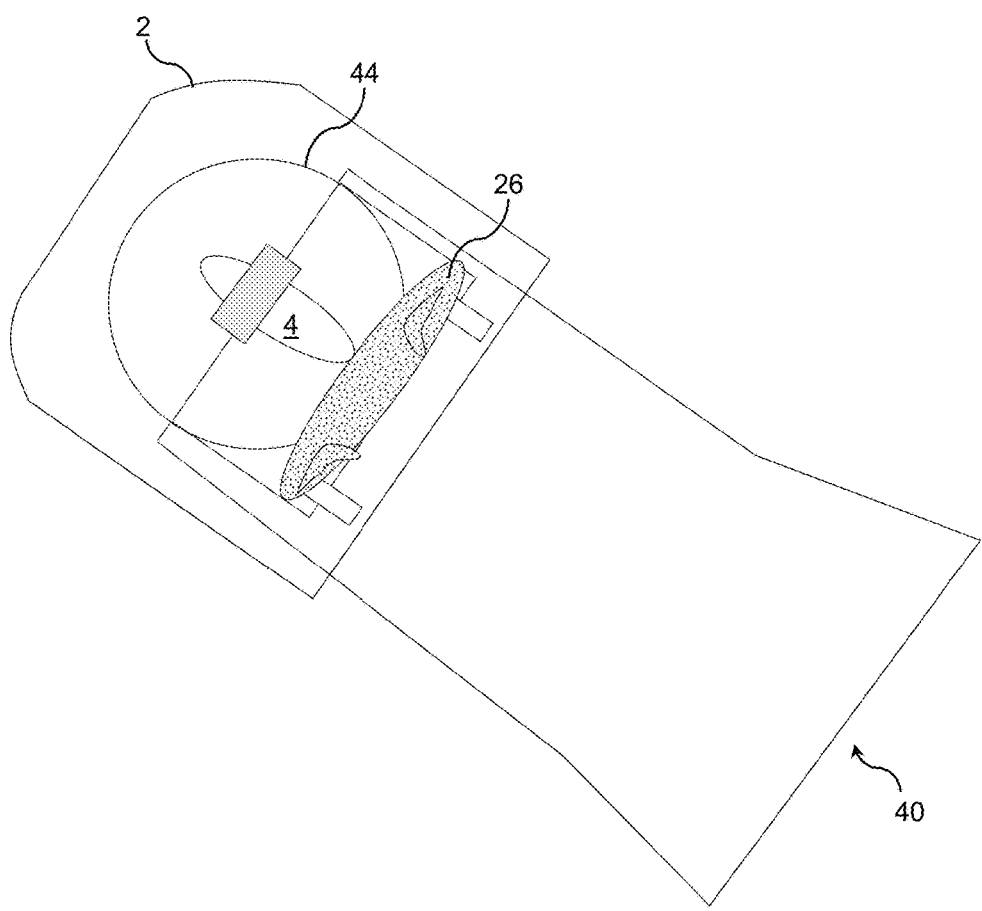
FIG. 7 shows a cross sectional view of an illustrative system according to an embodiment.

In an embodiment, as shown in FIG. 7, a rotating sphere 44 can be adjacent to the second compartment 26 in order to dispense a portion of the flowable product stored within the container 40. The ultraviolet radiation source(s) 4 can be located within the rotating sphere 44 and emit ultraviolet radiation directed towards the second compartment 26. The rotating sphere 44 can be made of an ultraviolet radiation transparent material, such as Teflon, and/or the like. The flowable product within the second compartment 26 can be readily disinfected by the ultraviolet radiation source(s) 4 and be made accessible to a user as the rotating sphere 44 rotates.

Figure 8:
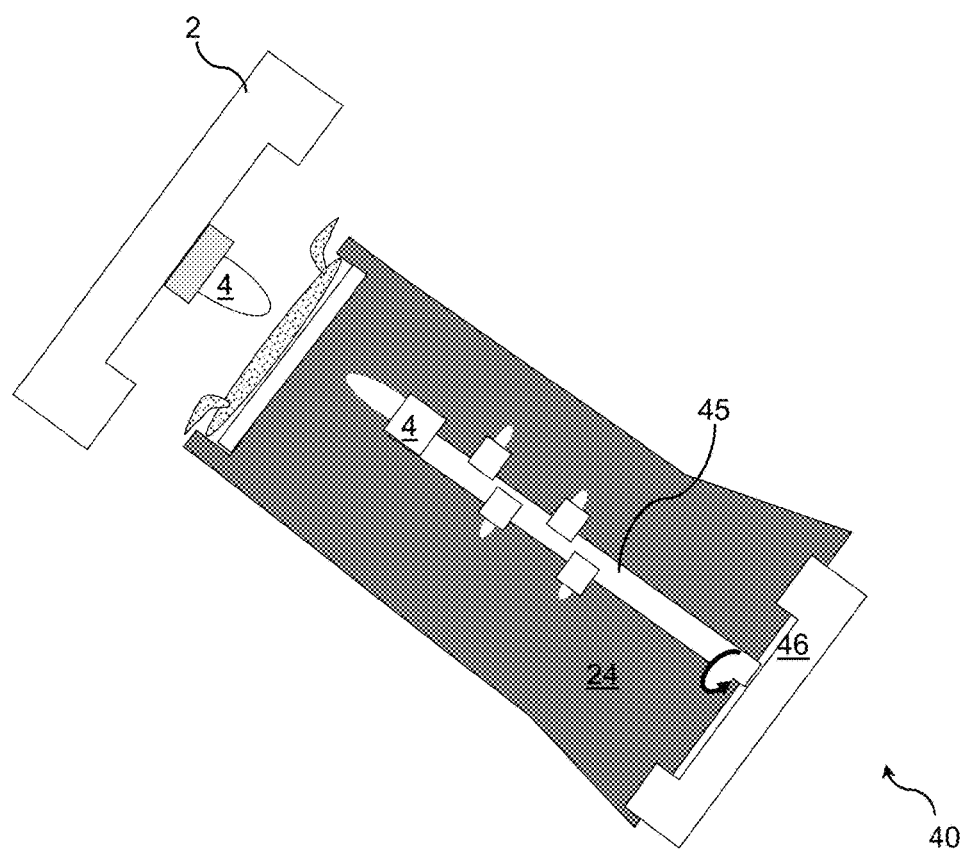
FIG. 8 shows a cross sectional view of an illustrative system according to an embodiment.
Figure 11:
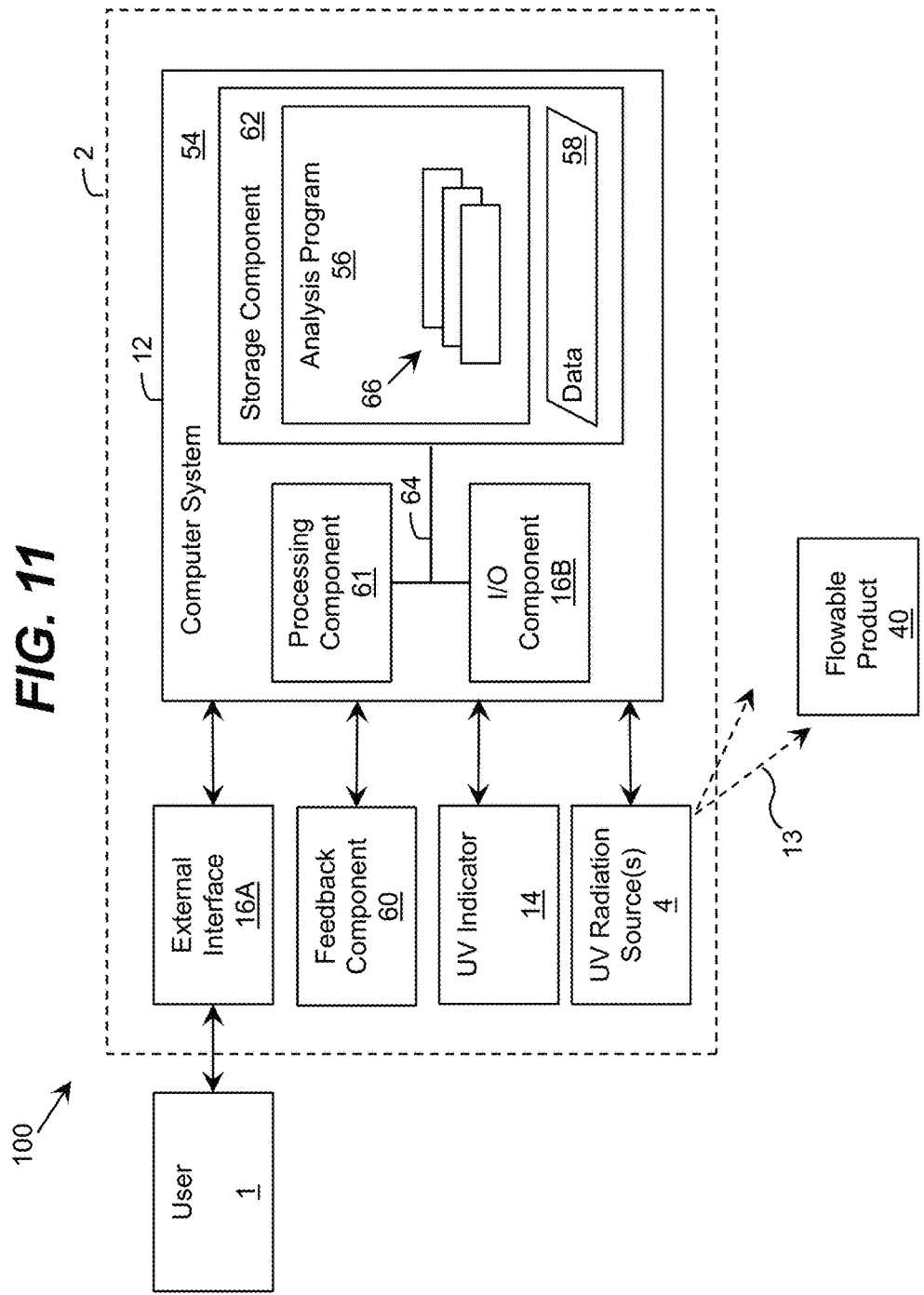
FIG. 11 shows an illustrative ultraviolet radiation system for a flowable product according to an embodiment.

In an embodiment, the flowable product stored within the first compartment 24 of a container 40 can also be disinfected. As seen in FIG. 8, the container 40 can include at least one ultraviolet radiation source(s) 4 located within the first compartment 24 of the container, e.g., mounted on a support trunk 45 within the first compartment 24 of the container 40. The support trunk 45 can be rotated by a nob 46 to effectively disinfect the flowable product stored within the first compartment 24. The nob 46 can be controlled manually by a user or automatically by a control system 12 (FIG. 1 and FIG. 11). The control system 12 also can control the ultraviolet radiation source(s) 4 mounted on the support trunk 45.

Figure 9:
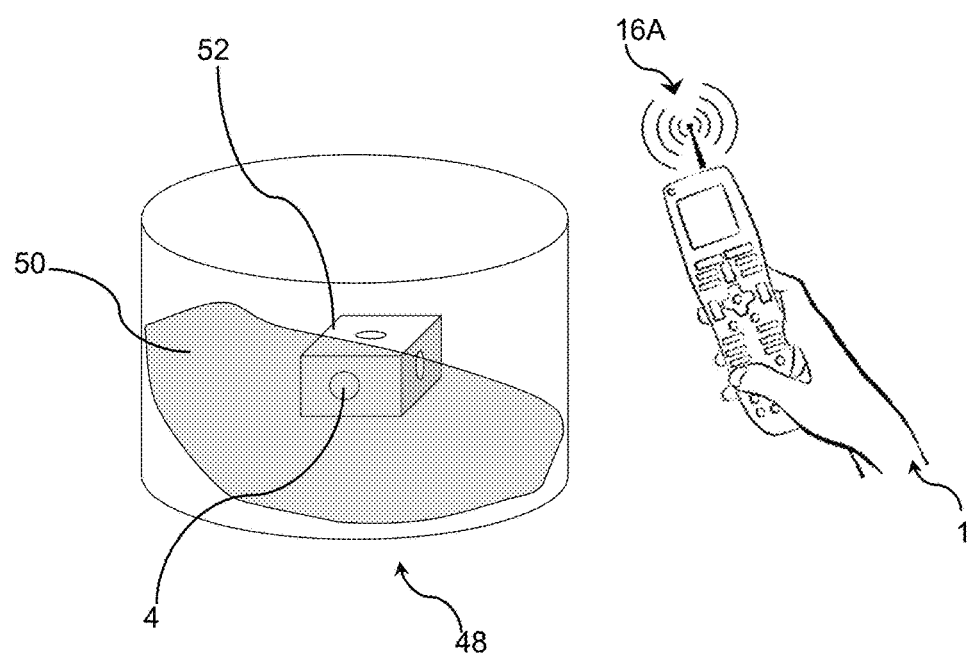
FIG. 9 shows an isometric view of an illustrative ultraviolet radiation system according to an embodiment.

Turning now to FIG. 9, an illustrative system including an ultraviolet radiation absorbing container 48 according to an embodiment is shown. In this embodiment, the container 48 includes a flowable product 50 to be disinfected stored therein. The system can include an inert enclosure 52 including a plurality of ultraviolet radiation source(s) 4, which can be placed within the container 48 in order to disinfect the flowable product 50 and/or the interior of the container 48. The inert enclosure 52 can include a control system (e.g., similar to the control system 12 in FIG. 11) to manage generation of the ultraviolet radiation. The system can also include an external control system for allowing a user to control one or more aspects of generating of the ultraviolet radiation. In an embodiment, a user 1 can control the ultraviolet radiation source(s) 4 using an external interface component 16A that can include a remote or a mobile device including software installed thereon (e.g., a mobile application or app), to control the ultraviolet radiation source(s) 4 through a wired or wireless communications channel. The inert enclosure 52 can include a sensor (not shown) for causing the ultraviolet radiation source(s) 4 to turn off when the inert enclosure 52 is not within the container 48 and/or the container 48 is not closed.

Turning now to FIGS. 10A-10C, illustrative flowable products for use with an ultraviolet radiation system according to an embodiment are shown. In FIG. 10A, the flowable product can comprise a bottle including a liquid to be disinfected. The cap 2 can include an ultraviolet radiation source 4. In FIG. 10B, the flowable product can include a highly reflective mixing element 7 for improving disinfection of the liquid within the bottle. The highly reflective mixing element 7 can be made of a reflective material, such as aluminum, and/or the like. In FIG. 10C, the flowable product can include additional ultraviolet radiation sources 4 in various locations along the interior surface of the bottle to increase an amount of ultraviolet radiation for disinfecting the liquid.

Turning now to FIG. 11, an illustrative ultraviolet radiation system 100 according to an embodiment is shown. In this case, the system 100 includes a monitoring and/or control system 12, which can be incorporated, for example, into the ultraviolet impermeable cap 2 (FIG. 2A). In this case, the monitoring and/or control system 12 can be embedded on a portion of the ultraviolet impermeable cap 2. The monitoring and/or control system 12 is shown implemented as a computer system 54 including an analysis program 56, which makes the computer system 54 operable to manage a set of ultraviolet radiation sources 4 (e.g., also mounted on the ultraviolet impermeable cap 2) by performing a process described herein. In particular, the analysis program 56 can enable the computer system 54 to operate the set of ultraviolet radiation sources 4 to generate and direct ultraviolet radiation 13 within an enclosed volume corresponding to a flowable product 40 and process data 58 corresponding to one or more attributes regarding the flowable product 40 and/or one or more attributes of the ultraviolet impermeable cap 2 (e.g., whether the ultraviolet impermeable cap 2 is off), which can be acquired by a feedback component 60. While a single ultraviolet radiation source 4 is shown in this figure, it is understood that the ultraviolet impermeable cap 2 can include any number of ultraviolet radiation sources 4 (e.g., mounted on the ultraviolet impermeable cap 2 and/or within the flowable product 40), the operation of which the computer system 54 can separately manage using a process described herein. In the case of more than one ultraviolet radiation source 4, it is understood that the computer system 54 can individually control each ultraviolet radiation source 4 and/or control two or more of the ultraviolet radiation sources 4 as a group. Furthermore, while ultraviolet radiation sources 4 are described herein, it is understood that the monitoring and/or control system 12 can operate one or more other types of devices, such as visible light LEDs, and/or the like.

In a more specific embodiment, the computer system 54 can control the ultraviolet radiation source(s) 4 such that the ultraviolet radiation sources operate at one or more wavelengths such that the power distribution over wavelength and illumination pattern/sequence are selected so that the properties of the flowable product exposed to the ultraviolet radiation are modified. The properties of the flowable product that are modified cannot be readily detectable without specialized equipment when illuminated by less than approximately two hours of continuous illumination. In an embodiment, the intrinsic properties with numerical values (e.g., color and viscosity) are modified by no more than approximately ten percent of their original value. The properties of the exposed product can include intrinsic properties (e.g., color, smell appearance, viscosity, and/or the like) or functional properties. The color property is measured by an RGB vector and the approximately ten percent threshold is attested by looking at the vector norm between two colors.

In an embodiment, during an initial period of operation (e.g., after the ultraviolet impermeable cap 2 is attached to a flowable product 40), the computer system 54 can acquire data from the feedback component 60 regarding one or more attributes of the flowable product 40 and generate data 58 for further processing. The data 58 can include a presence of biological activity (e.g., microorganisms, viruses, bacteria, and/or the like) within an enclosed area of the flowable product 40, a disinfection schedule history for the flowable product 40, a determination of whether the ultraviolet impermeable cap 2 is closed or open, and/or the like. The flowable product 40 can include any product that a user 1 desires to be disinfected. For example, the flowable product 40 can comprise a liquid, a colloid, a cream, a suspension, an emulsion, a powder and/or the like, and any accessories used in conjunction with the flowable product 40, including containers, caps, brushes, applicators, and/or the like. For example, illustrative flowable products 40 can include toothpaste, creams, lotions, cosmetics (e.g., lipstick, eyeliner, powder compacts, and/or the like), brushes, and/or the like. The computer system 54 can use the data 58 to control one or more aspects of the ultraviolet radiation generated by the ultraviolet radiation source(s) 4.

Furthermore, one or more aspects of the operation of the ultraviolet radiation source 4 can be controlled by a user 1 via an external interface component 16A. The external interface component 16A can be located on an exterior portion of the ultraviolet impermeable cap 2 and allow the user 1 to choose when to turn on the ultraviolet radiation source 4. However, it is understood that the monitoring and/or control system 12 (e.g., via a sensor and/or switch 6 shown in FIG. 1) must still determine that the ultraviolet impermeable cap 2 is closed (e.g., attached to the flowable product 40) prior to turning on the ultraviolet radiation source 4 to avoid harming the user 1. In addition to showing statistical information regarding the flowable product 40 to the user 1, the external interface component 16A can include a touch screen that shows control dials for adjusting an intensity, scheduling, and other operational properties of the at least one ultraviolet radiation source 4. In an embodiment, the external interface component 16A can include a touchscreen, a keyboard, a plurality of buttons, a joystick-like control mechanism, and/or the like, to control the at least one ultraviolet radiation source 4. In an alternative embodiment, the external interface component 16A can be separate from the ultraviolet impermeable cap 2. For example, the external interface component 16A can include a remote or a mobile device including a software installed on the operating system thereon, to control the ultraviolet radiation source(s) 4. Such a component 16A can communicate with the remaining portions of the control system 12 wirelessly, via Wi-Fi, Bluetooth, and/or the like. In an illustrative embodiment, the external interface component 16A comprises a personal mobile device, such as a mobile phone, or the like, which includes an ability (e.g., via a mobile app installed thereon) to communicate with the control system 12 using a wireless communications solution.

The computer system 54 is shown including a processing component 61 (e.g., one or more processors), a storage component 62 (e.g., a storage hierarchy), an input/output (I/O) component 16B (e.g., one or more I/O interfaces and/or devices), and a communications pathway 64. In general, the processing component 61 executes program code, such as the analysis program 56, which is at least partially fixed in the storage component 62. While executing program code, the processing component 61 can process data, which can result in reading and/or writing transformed data from/to the storage component 62 and/or the I/O component 16B for further processing. The pathway 64 provides a communications link between each of the components in the computer system 54. The I/O component 16B and/or the external interface component 16A can comprise one or more human I/O devices, which enable a human user 1 to interact with the computer system 54 and/or one or more communications devices to enable a system user 1 to communicate with the computer system 54 using any type of communications link. To this extent, during execution by the computer system 54, the analysis program 56 can manage a set of interfaces (e.g., graphical user interface(s), application program interface, and/or the like) that enable human and/or system users 1 to interact with the analysis program 56. Furthermore, the analysis program 56 can manage (e.g., store, retrieve, create, manipulate, organize, present, etc.) the data, such as data 36, using any solution.

In any event, the computer system 54 can comprise one or more general purpose computing articles of manufacture (e.g., computing devices) capable of executing program code, such as the analysis program 56, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 56 can be embodied as any combination of system software and/or application software.

Furthermore, the analysis program 56 can be implemented using a set of modules 66. In this case, a module 66 can enable the computer system 54 to perform a set of tasks used by the analysis program 56, and can be separately developed and/or implemented apart from other portions of the analysis program 56. When the computer system 54 comprises multiple computing devices, each computing device can have only a portion of the analysis program 56 fixed thereon (e.g., one or more modules 66). However, it is understood that the computer system 54 and the analysis program 56 are only representative of various possible equivalent monitoring and/or control systems 12 that may perform a process described herein. To this extent, in other embodiments, the functionality provided by the computer system 54 and the analysis program 56 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 12 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 54. However, it is understood that the functionality described in conjunction therewith can be implemented by any type of monitoring and/or control system 12.

Regardless, when the computer system 54 includes multiple computing devices, the computing devices can communicate over any type of communications link. Furthermore, while performing a process described herein, the computer system 54 can communicate with one or more other computer systems, such as the user 1, using any type of communications link. In either case, the communications link can comprise any combination of various types of wired and/or wireless links; comprise any combination of one or more types of networks; and/or utilize any combination of various types of transmission techniques and protocols.

The system 100 also can include an ultraviolet radiation indicator 14 (e.g., an LED), which can be operated by the computer system 54 to indicate when ultraviolet radiation 13 is being generated and directed at the flowable product 40. The ultraviolet radiation indicator 14 can include one or more LEDs for emitting a visual light for the user 1. In another embodiment, the ultraviolet radiation indicator 14 can include a sound or a vibration for a predetermined amount of time to indicate that ultraviolet radiation 13 is being and/or is no longer being generated at the flowable product 40.

Figure 12:
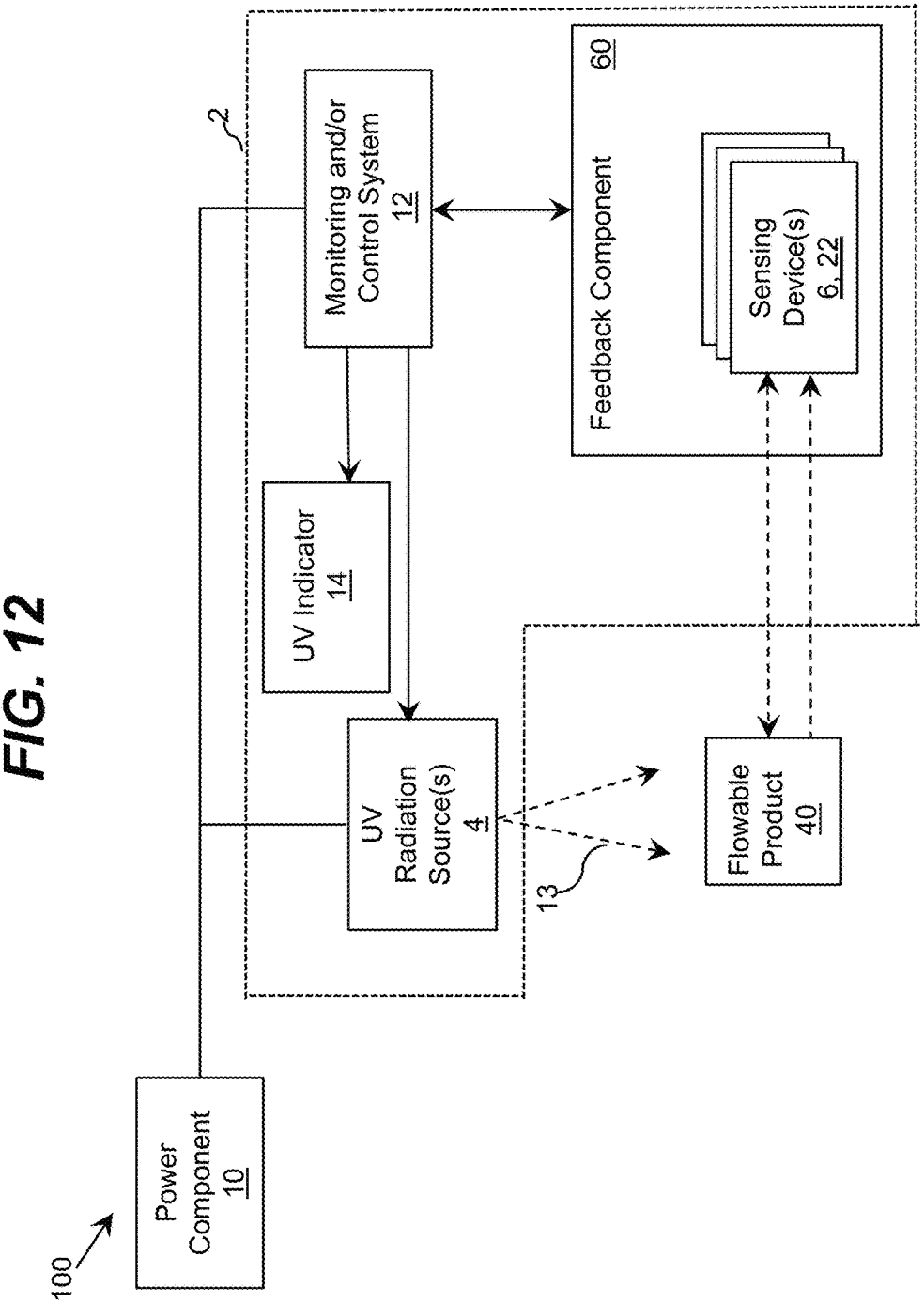
FIG. 12 shows an illustrative system including an ultraviolet radiation system for a flowable product according to an embodiment.

Turning now to FIG. 12, an illustrative system including an ultraviolet radiation system 100 for a flowable product 40 is shown. The ultraviolet radiation system 100 is shown including ultraviolet radiation source(s) 4 (mounted on an ultraviolet impermeable cap 2 as shown in FIG. 1). The monitoring and/or control system 12 is configured to control the ultraviolet radiation source(s) 4 to direct ultraviolet radiation 13 at the enclosed volume corresponding to the flowable product 40. The feedback component 60 is configured to acquire attribute data used by the monitoring and/or control system 12 to manage the ultraviolet radiation source(s) 4. As illustrated, the feedback component 60 can include a plurality of sensing devices 6, each of which can acquire attribute data used by the monitoring and/or control system 12 to control and manage the ultraviolet radiation source(s) 4.

The attribute data acquired by the feedback component 60 can include any combination of a plurality of attributes of the flowable product 40 located therein. Illustrative attributes for the flowable product 4 can include: a presence of biological activity in an enclosed area of the flowable product 40, a determination of whether the ultraviolet impermeable cap 2 is open or closed, a change in the physical appearance of the flowable product 40 subjected to ultraviolet radiation 13, and/or the like. A sensing device can include a sensor and/or a switch 6 (FIG. 1) configured to sense that the ultraviolet impermeable cap 2 is physically closed (e.g., attached to the flowable product 40) before the monitoring and/or control system 12 turns on the ultraviolet radiation source(s) 4. Furthermore, the sensing device can include a sensor 22 (FIG. 1) that can sense that biological activity is present within the enclosed area of the flowable product 40 before the monitoring and/or control system 12 turns on the ultraviolet radiation source(s) 4.

In the case of determining a presence of biological activity within the enclosed volume corresponding to the flowable product 40, the sensing devices (e.g., sensor 22)

can also determine a location of the biological activity, a type of biological activity (e.g., type of organism), a concentration of the biological activity, an estimated amount of time an organism has been in a growth phase (e.g., exponential growth and/or stationary), and/or the like. Furthermore, the sensor 22 can determine information on the variation of the biological activity over time, such as a growth rate, a rate with which an area including the biological activity is spreading, and/or the like. In an embodiment, a set of biological activity dynamics are related to various attributes of bacteria and/or virus activity within the enclosed volume corresponding to the flowable product 40, including, for example, the presence of detectable bacteria and/or virus activity, measured bacteria and/or virus population/concentration time dynamics, growth phase, and/or the like.

In an embodiment, to determine the presence of biological activity within the enclosed volume corresponding to the flowable product 40, the sensor 22 can include at least one of a visual camera or a chemical sensor. The visual camera can acquire visual data (e.g., visual, electronic, and/or the like) used to monitor the enclosed volume corresponding to the flowable product 40, while the chemical sensor can acquire chemical data (e.g., chemical, electronic, and/or the like) used to monitor the enclosed area of the flowable product 40. For example, when the monitoring and/or control system 12 is operating the ultraviolet radiation source 4, a visual camera and/or a chemical sensor 22 monitoring the enclosed volume corresponding to the flowable product 40 may be operated to detect the presence of microorganisms. In a specific embodiment, the visual camera 22 comprises a fluorescent optical camera that can detect bacteria and/or viruses that become fluorescent under ultraviolet radiation. However, it is understood that a visual camera and a chemical sensor are only illustrative of various types of sensors that can be implemented. For example, the sensor 22 can include one or more mechanical sensors (including piezoelectric sensors, various membranes, cantilevers, a micro-electromechanical sensor or MEMS, a nanomechanical sensor, and/or the like), which can be configured to acquire any of various types of data regarding the enclosed volume corresponding to the flowable product 40.

The monitoring and/or control system 12 can be configured to control and adjust a direction, an intensity, a pattern, and/or a spectral power (e.g., wavelength) of the at least one ultraviolet radiation source 4, based on attribute data acquired by the feedback component 60. The monitoring and/or control system 12 can control and adjust each property of the ultraviolet radiation source 4 independently. For example, the monitoring and/or control system 12 can adjust the intensity, time duration, and/or time scheduling (e.g., including duration (e.g., exposure/illumination time)), duty cycle, time between exposures/illuminations, and/or the like) of the ultraviolet radiation source 4 for a given wavelength. Each of the properties of the ultraviolet radiation source 4 can be adjustable and controlled by the monitoring and/or control system 12 according to data provided by the feedback component 60.

The monitoring and/or control system 12 can also be configured to adjust the direction of the ultraviolet radiation 13 according to a location of the biological activity detected on the flowable product 40 within the enclosed area by the sensor 22 using any solution. The monitoring and/or control system 12 can be configured to utilize a target timing, intensity, and/or spectral power of the ultraviolet radiation according to a type of biological activity. That is, the sensor 22 can sense locations of higher levels of biological activity on specific areas on the flowable product 40, and the ultraviolet radiation source 4 can be configured by the monitoring and/or control system 12 to direct higher doses (by increasing intensity or exposure) of ultraviolet radiation at those particular areas on flowable product 40 with higher levels of biological activity (e.g., non-uniform ultraviolet radiation).

The sensing devices can also include a sensor 6 that can sense that the ultraviolet impermeable cap 2 is physically open or closed (e.g., unattached or attached to the flowable product 40). In response to detecting that the ultraviolet impermeable cap 2 is closed (e.g., attached to the flowable product 40), the monitoring and/or control system 12 can be configured to automatically turn on the ultraviolet radiation 13. In one embodiment, the monitoring and/or control system 12 can be configured to set a periodic or an aperiodic schedule for the ultraviolet radiation when the ultraviolet impermeable cap 2 is closed. This (periodic or aperiodic) schedule can be interrupted when the sensor 6 senses that the ultraviolet impermeable cap 2 is opened (e.g., unattached to the flowable product 40) and the monitoring and/or control system 2 can be configured to turn off the ultraviolet radiation. In this case, the schedule (periodic or aperiodic) can be resumed once the sensor 6 senses the ultraviolet impermeable cap 2 is closed again.

The feedback component 60 can also include a sensing device (e.g., sensor 22) that can sense a change in the color, smell, conductive properties, and/or the like of the flowable product 40 within the enclosed area. In response to a change that exceeds a threshold, the monitoring and/or control system 12 can be configured to adjust the ultraviolet radiation 13 accordingly. For example, an intrinsic property (e.g., color and/or viscosity) of the flowable product 40 can be modified by no more than approximately ten percent of the original value for the flowable product 40.

It is understood that the system 100 may include a power component 10 to supply power to one or more of the various components of system 100, such as ultraviolet radiation sources 4, feedback component 60, monitoring and/or control system 12, and/or the like. The power component 10 can be separate from the ultraviolet impermeable cap 2 (e.g., an electrical cord enabling power to be obtained via an electric grid (e.g., a household outlet), as seen in FIG. 2A), or include be included with t ultraviolet impermeable cap 2 (e.g., rechargeable batteries). The power component 10 can comprise any source of power including, but not limited to, a battery set, a solar cell, another electronic device (e.g., via a universal serial bus (USB) connection), and/or the like. For example, the power component 10 can include any of various types of rechargeable batteries (e.g., lithium ion, nickel-cadmium, and/or the like). The power component 10 can be configured for operation of high efficiency direct current (DC) step-up/boost converters. In an embodiment, the power component (e.g., conversion efficiency and maximum battery life) is configured (e.g., optimized) to keep a difference between the electrical power available versus the electrical power required for the various components at the minimum. In an embodiment, the power component comprises a battery set that is capable of being recharged through a typical household outlet. A charging system for this embodiment can comprise an electrical cord for charging that can include, for example, a cord with a USB connection, which can enable charging and communications with an external computing device.

For each embodiment of the ultraviolet impermeable cap 2 including the ultraviolet radiation source(s) 4, the ultraviolet impermeable cap 2 can be configured to provide at least a target amount of mechanical protection for the flowable product 40 attached to the ultraviolet impermeable cap 2. For example, the target amount of mechanical protection can provide at least ten feet drop protection for the flowable product 40 attached to the ultraviolet impermeable cap 2, which can be measured by a drop test. The drop test can include dropping the ultraviolet impermeable cap 2 attached to the flowable product 40 from a height of approximately ten feet. This drop test can be performed multiple times, while capturing images of the landing each time. The flowable product 40 attached to the ultraviolet impermeable cap 2 can be examined after each drop to ensure the no significant damage has occurred. In an embodiment, portions of an exterior of the ultraviolet impermeable cap 2 can include a material that absorbs the impact from the drop. For instance, portions of the exterior of the ultraviolet impermeable cap 2 can be made of rubber or plastic. Additionally, the material can rubberized polycarbonate, polycarbonate, an acrylonitrile butadiene styrene (ABS) composite, polyurethane composites, and/or the like.

Figure 13B:
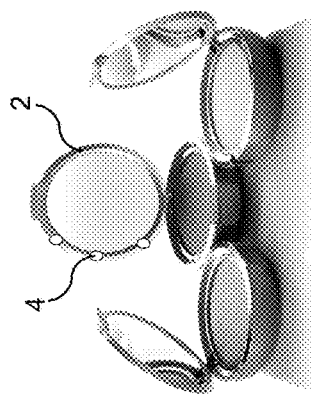
FIGS. 13A-13C show illustrative flowable products for use with an ultraviolet radiation system according to embodiments.
Figure 13C:
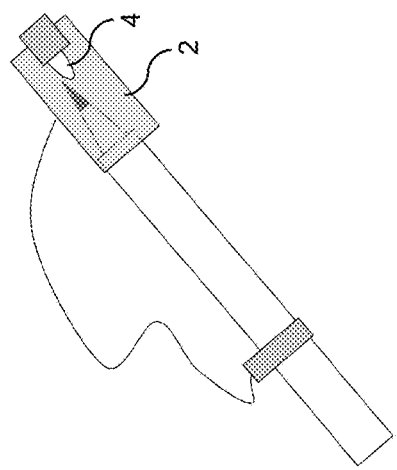
Figure 13A:
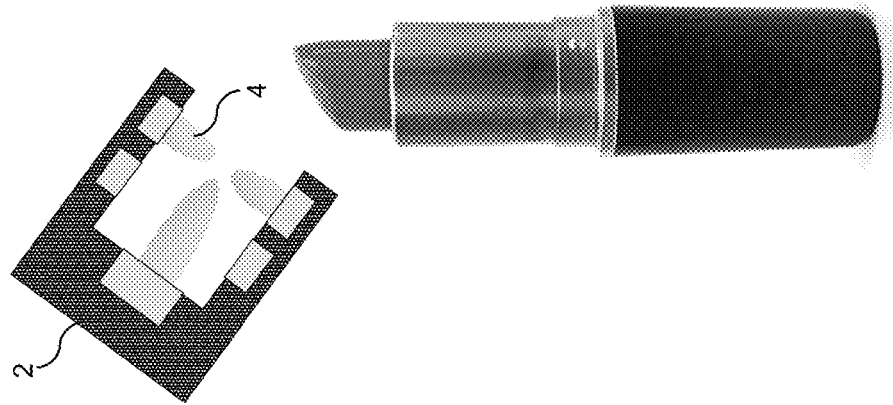

As described herein, embodiments of the ultraviolet impermeable cap 2 can be implemented to be a part of any type of flowable product 40. FIGS. 13A-13C show illustrative flowable products 40 for use with an ultraviolet radiation system 100 (FIG. 11) according to embodiments. For example, the ultraviolet impermeable cap 2 can be attached to a lipstick (FIG. 13A). Alternatively, the ultraviolet impermeable cap 2 can be attached to a powder compact (FIG. 13B). The ultraviolet impermeable cap 2 can be attached to a cosmetic pencil (FIG. 13C), and/or the like. In each case, an embodiment of the system 100 can be implemented in conjunction therewith using any solution. To this extent, it is understood that embodiments of the system 100 can vary significantly in the number of devices, the size of the devices, the power requirements for the system, and/or the like. Regardless, it is understood that these are only exemplary flowable products and that the system 100 may be applicable to other flowable products not specifically mentioned herein.

While shown and described herein as a method and system for disinfecting an volume corresponding to a flowable product, it is understood that aspects of the invention further provide various alternative embodiments. For example, in one embodiment, the invention provides a computer program fixed in at least one computer-readable medium, which when executed, enables a computer system to disinfect a flowable product using a process described herein. To this extent, the computer-readable medium includes program code, such as the analysis program 56 (FIG. 11), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 56 (FIG. 11), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for disinfecting a volume corresponding to a flowable product. In this case, the generating can include configuring a computer system, such as the computer system 54 (FIG. 11), to implement a method of disinfecting a flowable product as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An apparatus, comprising:
   an ultraviolet radiation containing case configured to enclose a volume corresponding to a flowable product, the case including a first compartment configured to store a first portion of the flowable product and a second compartment configured to store a second portion of the flowable product, wherein one of the first portion or the second portion of the flowable product can be accessed when the case is open;
   a rotatable support trunk located within the first compartment;
   a plurality of ultraviolet radiation sources mounted on the rotatable support trunk, wherein the plurality of ultraviolet radiation sources are configured to emit radiation onto the first portion of the flowable product;
   a cover configured to selectively close and open the case; and
   a sensor configured to cause the plurality of ultraviolet radiation sources to turn off when the cover is removed from the case.

2. The apparatus of claim 1, wherein the plurality of ultraviolet radiation sources mounted on the rotatable support trunk are configured to emit radiation onto the flowable product during rotation of the support trunk.

3. The apparatus of claim 1, further comprising a control system configured to control disinfection of the first portion of the flowable product with the plurality of ultraviolet radiation sources.

4. The apparatus of claim 3, wherein the support trunk includes a nob that effectuates rotation of the support trunk within the first compartment of the case.

5. The apparatus of claim 4, wherein the nob is operatively coupled to the control system, the nob automatically rotating the support trunk within the first compartment of the case at the direction of the control system.

6. The apparatus of claim 1, wherein the second portion of the flowable product can be accessed when the case is open, and wherein the cover includes an ultraviolet radiation source to disinfect the second portion of the flowable product in the second compartment of the case.

7. The apparatus of claim 1, further comprising at least one one-way channel to transfer a portion of the flowable product from the first compartment to the second compartment.

8. The apparatus of claim 1, wherein the cover is ultraviolet impermeable.

9. The apparatus of claim 1, further comprising an interconnect positioned between the case and the cover to form an interconnection therebetween.

10. The apparatus of claim 1, further comprising at least one reflector mounted on an interior surface of at least one of: the case or the cover for reflecting the ultraviolet radiation.

11. An apparatus, comprising:
an ultraviolet radiation containing case configured to enclose a volume corresponding to a flowable product, the case including a first compartment configured to store a first portion of the flowable product and a second compartment configured to store a second portion of the flowable product, wherein one of the first portion or the second portion of the flowable product can be accessed when the case is open;
a rotating auger configured to transfer the flowable product from the first compartment to the second compartment, the rotating auger having a first end extending into the first compartment and a second end extending into the second compartment;
a cover configured to selectively close and open the case; and
at least one ultraviolet radiation source mounted on at least one of: the case or the cover to generate ultraviolet radiation for disinfecting the flowable product.

12. The apparatus of claim 11, wherein the case includes a separation plate that separates the first compartment from the second compartment.

13. The apparatus of claim 12, wherein the separation plate moves vertically in the case as a function of the rotation of the rotating auger.

14. The apparatus of claim 11, further comprising at least one one-way channel to transfer a portion of the flowable product from the first compartment to the second compartment.

15. The apparatus of claim 14, wherein rotation of the rotating auger pushes portions of the flowable product from the first compartment through the at least one one-way channel into the second compartment.

16. The apparatus of claim 11, further comprising a control system configured to control disinfection of the flowable product with the at least one ultraviolet radiation source.

17. The apparatus of claim 16, further comprising at least one sensor to obtain attribute information regarding biological activity in the flowable product, the control system controlling and adjusting at least one of an irradiating direction, an intensity, a pattern, or a spectral power, of the at least one ultraviolet radiation source, based on attribute information acquired by the at least one sensor.

18. A system, comprising:
an ultraviolet radiation containing case including a flowable product stored therein;
an inert enclosure located inside the ultraviolet radiation containing case, the inert enclosure including at least one ultraviolet radiation source mounted thereon that is configured to emit ultraviolet radiation onto at least one of the flowable product or an interior of the ultraviolet radiation containing case, and a control system configured to control operation of the at least one ultraviolet radiation source; and
an external controller operatively coupled to the inert enclosure, the external controller configured to allow an operator to remotely control disinfection of the flowable product and the interior of the ultraviolet radiation containing case with the inert enclosure, the external controller having a communication channel with the control system in the inert enclosure that permits the operator to remotely control operation of the at least one ultraviolet radiation source for disinfection of the at least one of the flowable product or the interior of the ultraviolet radiation containing case.

19. The system of claim 18, wherein the external controller includes a wireless controller.

20. The system of claim 18, wherein the inert enclosure further includes a sensor operatively coupled to the control system in the inert enclosure, wherein the sensor is configured to detect when the inert enclosure is no longer enclosed by the ultraviolet radiation containing case, and the control system is configured to turn off the at least one ultraviolet radiation source in response to the sensor detecting that the inert enclosure is no longer enclosed by the ultraviolet radiation containing case.

* * * * *